(12) United States Patent
Pelta et al.

(10) Patent No.: US 11,002,657 B2
(45) Date of Patent: May 11, 2021

(54) ELECTRICAL DETECTION PROCESS FOR PEPTIDES, PROTEINS AND OTHER MACROMOLECULES

(71) Applicants: EXCILONE, Elancourt (FR);
UNIVERSITÉ DE CERGY PONTOISE, Cergy Pontoise (FR);
UNIVERSITÉ EVRY VAL D'ESSONNE, Evry (FR);
ASSISTANCE PUBLIQUE-HÔPITAUX DE PARIS, Paris (FR)

(72) Inventors: Juan Pelta, Elancourt (FR);
Abdelghani Oukhaled, Elancourt (FR);
Philippe Manivet, Elancourt (FR);
Fabien Piguet, Elancourt (FR); Hadjer Ouldali, Elancourt (FR); Zuzana Krupova, Elancourt (FR); Pierre Defrenaix, Elancourt (FR)

(73) Assignees: EXCILONE, Elancourt (FR);
UNIVERSITÉ DE CERGY PONTOISE, Cergy Pontoise (FR);
UNIVERSITÉ EVRY VAL D'ESSONNE, Evry (FR);
ASSISTANCE PUBLIQUE-HÔPITAUX DE PARIS, Paris (FR)

( * ) Notice: Subject to any disclaimer, the term of this patent is extended or adjusted under 35 U.S.C. 154(b) by 156 days.

(21) Appl. No.: 16/313,349

(22) PCT Filed: Jun. 26, 2017

(86) PCT No.: PCT/FR2017/000129
§ 371 (c)(1),
(2) Date: Dec. 26, 2018

(87) PCT Pub. No.: WO2017/220875
PCT Pub. Date: Dec. 28, 2017

(65) Prior Publication Data
US 2019/0317006 A1    Oct. 17, 2019

(30) Foreign Application Priority Data
Jun. 24, 2016  (FR) ..................... 16.01007

(51) Int. Cl.
*G01N 27/327* (2006.01)
*G01N 33/487* (2006.01)
*G01N 15/12* (2006.01)

(52) U.S. Cl.
CPC ......... *G01N 15/12* (2013.01); *G01N 27/3278* (2013.01); *G01N 33/48721* (2013.01)

(58) Field of Classification Search
CPC ................. G01N 27/3278; G01N 33/48721
See application file for complete search history.

(56) References Cited

U.S. PATENT DOCUMENTS

| | | | | |
|---|---|---|---|---|
| 2015/0060277 A1* | 3/2015 | Golovchenko | ... | B01L 3/502761 204/453 |
| 2016/0053300 A1* | 2/2016 | Maglia | ............... | G01N 27/3278 435/6.1 |

OTHER PUBLICATIONS

Pastoriza-Gallego et al., "Dynamics of Unfolded Protein Transport through an Aerolysin Pore,"J. Am. Chem. Soc. 2011, 133, 2923-2931 with Supporting Information appended (Year: 2011).*

(Continued)

*Primary Examiner* — Alexander S Noguerola
(74) *Attorney, Agent, or Firm* — Oliff PLC

(57) ABSTRACT

An aerolysin nanopore or a nanotube is used for the electrical detection of peptides, proteins separated by at least one amino acid and other macromolecules such as polysaccharides or synthetic or natural polymers present in a preparation where said nanopore or nanotube is inserted into a lipid membrane which is subjected to a difference in potential (Continued)

greater than −160 mV, in a reaction medium having an alkali metal halide electrolyte solution with a concentration of less than 6M and at a temperature of less than 40° C., and where said use is intended to differentiate said peptides, proteins and other molecules according to their length and their mass. Application to the sequencing of peptides and other molecules to differentiate them according to their length and mass with an amino acid-level or monomer-level resolution and to medical diagnosis.

20 Claims, 8 Drawing Sheets

(56) References Cited

OTHER PUBLICATIONS

Stefureac et al., "Transport of α-Helical Peptides through α-Hemolysin and Aerolysin Pores," Biochemistry 2006, 45, 9172-9179 (Year: 2006).*
Wilmsen et al., "Aerolysin, a Hemolysin from Aeromonas hydrophila, Forms Voltage-Gated Channels in Planar Lipid Bilayers," J. Membrane Biol. 115, 71-81 (1990) (Year: 1990).*
Zhao et al.,"Stochastic Study of the Effect of Ionic Strength on Noncovalent Interactions in Protein Pores," Biophysical Journal vol. 94 Feb. 2008 1267-1275 (Year: 2008).*
Aksimentievetal., "Imaging α-Hemolysin with Molecular Dynamics: ionic Conductance, Osmotic permeability, and the Electrostatic Potential Map," Biophysical Journal vol. 88 Jun. 2005 3745-3761 (Year: 2005).*
Cao et al., "Discrimination of oligonucleotides of different lengths with a wild-type aerolysin nanopore,", including Supplemental Information, Nature Nanotechnology published online Apr. 25, 2016 (Year: 2016).*
Clark et al, "Continuous Base Identification for Single-Molecule Nanopore DNA Sequencing," Nature Nanotechnology, vol. 4, No. 4, Apr. 1, 2009, pp. 265-270.
Nivala et al, "Discrimination Among Protein Variants Using an Unfoldase-Coupled Nanopore," ACS Nano, vol. 8, No. 12, Nov. 17, 2014, pp. 12365-12375.
Cao et al, "Discrimination of Oligonucleotides of Different Lengths with a Wild-Type Aerolysin Nanopore," Nature Nanotechnology, vol. 11, No. 8, Apr. 25, 2016, pp. 713-719.
Piguet et al, "Electroosmosis Through a-Hemolysin that Depends on Alkali Cation Type," Journal of Physical Chemistry Letters, vol. 5, No. 24, Dec. 1, 2014, pp. 4362-4367.
Boulon et al, "Establishment of a Protein Frequency Library and Its Application in the Reliable Identification of Specific Protein Interaction Partners", Molecular & Cellular Proteomics, vol. 9, No. 5, Dec. 20, 2009, pp. 861-879.
Fennouri et al, "Kinetics of Enzymatic Degradation of High Molecular Weight Polysaccharides through a Nanopore: Experiments and Data-Modeling," Analytical Chemistry, vol. 85, No. 18, Aug. 30, 2013, pp. 8488-8492.
Wang et al, "Nanopore Sensing of Botulinum Toxin B by Discriminating an Enzymatically Cleaved Peptide from a Synaptic Protein Synaptobrevin 2 Derivative," ACS Applied Materials & Interfaces, vol. 7, No. 1, Dec. 16, 2014, pp. 184-192.
Martin et al, "Principles of Protein Targeting to the Nucleolus," Nucleus, vol. 6, No. 4, Jul./Aug. 2015, pp. 314-325.
Oukhaled et al, "Sensing Proteins Through Nanopores: Fundamental to Applications," ACS Chemical Biology, vol. 7, No. 12, Nov. 11, 2012, pp. 1935-1949.
Sep. 29, 2017 International Search Report issued in PCT Application No. PCT/FR2017/000129.
Jan. 8, 2018 Written Opinion issued in PCT Application No. PCT/FR2017/000129.

* cited by examiner (a)

(b)

(c)

(d)

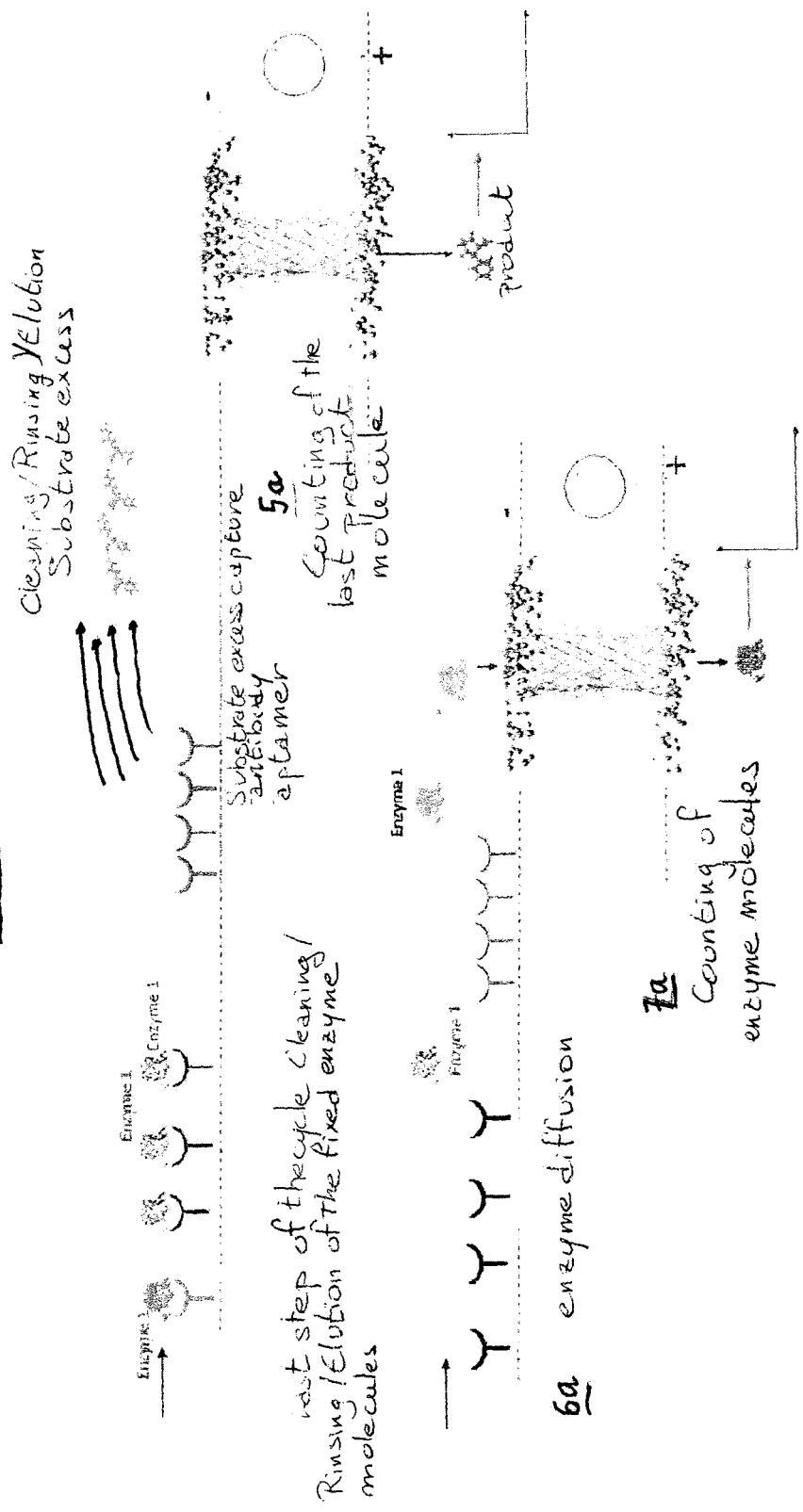

ELECTRICAL DETECTION PROCESS FOR PEPTIDES, PROTEINS AND OTHER MACROMOLECULES

FIELD

The technical scope of the present invention is that of the electrical detection of molecules in a mixture.

BACKGROUND

The principle of the electrical detection of the transport of molecules through a nanopore that may be a protein channel or nanotube inserted into a lipid membrane or nanometric hole pierced in a solid membrane is well known.

The membrane is subjected to a difference in potential that induces an ionic current through the nanopore in the presence of an electrolyte solution. The passage of a molecule through the nanopore, or the interaction of the molecule with the nanopore, induces a measurable drop in the current. The amplitude of this drop and its duration depend, in particular, on the conformation of the molecule, its size, sequence and chemical nature.

This sensitivity has been used to perform ultra-fast DNA sequencing (Branton et al, 2008, Nat. Biotech or Karlsson et al, 2015, Scientific reports).

Another, very promising, application relates to the possibility of determining the size or the mass of a molecule or a mixture of molecules thus performing mass spectrometry using a nanopore coupled with an ultra-sensitive electrical detection system.

The separation of a mixture of synthetic polymers has been demonstrated (Roberston et al, 2007, PNAS; Reiner et al, 2010, PNAS; Baaken et al, 2011, ACS Nano; Baaken et al, 2014, ACS Nano) wherein one chain size corresponds to an electrical current blockade signature. Recently, the separation of nucleotides between 2 and 10 monomers was observed for only one pure poly-desoxyadenosine, through an aerolysin nanopore (Cao et al, 2016, Nat. nanotech).

The use of the aerolysin nanopore is well known and Wilmsen et al, 1990, showed that the aerolysin formed a channel sensitive to electrical current in a lipid bilayer.

The document written by Stefureac et al, 2006, relates to the transport of peptides through aerolysin pores. Peptides of different lengths were observed, as were the differences in current blockade durations but no fine resolution was reached on an amino acid level.

The documents by Pastoriza-Gallego et al, JACS 2011 and Payet et al, Anal. Chem. 2012, relate to the dynamics of non-folded proteins (conformations) through an aerolysin nanopore. These studies essentially related to the determination of the conformations of big proteins (>370 amino acids) with the aerolysin associated with different current blockade durations. However, no fine resolution was proposed to distinguish two peptides or two proteins that differ by only a single amino acid.

SUMMARY

Examination of the abundant available literature in this domain shows that there are difficulties in separating either small or large polypeptide chains, a separation problem that has not been resolved to this day. The only fine resolution to visualize aromatic enantiomers (Tryptophane, Phenylalanin, Tyrosine) was made possible after chemical modification of an alpha-hemolysin pore (Boersma and Bayley, 2012, Angew. Chem. Int.Ed).

The inventers thus imagined the use of an aerolysin protein channel, in precise physical-chemical conditions so as to isolate the small chains of a few monomers without having to proceed with costly and complex modifications to the aerolysin nanopore.

With regard to peptides or proteins, numerous works have been published on the macroscopic determination of the size of a protein by using the transport time (current blockade duration) or the current blockade depth with solid nanopores (Han et al, 2006, APL; Fologea et al, 2007, APL; Cressiot et al, 2011, ACS Nano; Plesa et al, 2013, Nanoletters, Freedman e al, 2013, Scientific reports; Larkin et al, 2014, BJ, Waduge et al, 2017) or with glass nanocapillaries (Li et al, 2013, ACS Nano; Steinbock et al, 2014, Nanoscale). If these approaches enable native proteins to be separated depending on their size, the proteins must differ by at least 4 kDa for the small chains and by more than 50 kDa for the long chains (Li et al, 2013, ACS Nano; Steinbock et al, 2014).

To date, the possibility has never been proven of separating peptides according to their size and mass by using aerolysin nanopores with a resolution enabling the inclusion of an amino acid in the chain to be determined.

It is precisely the purpose of the invention to propose the use of a nanopore and a process enabling the identification of peptides, proteins, polysaccharides or synthetic polymers present in a mixture.

The invention thus relates to the use of an aerolysin nanopore or a nanotube for the electrical detection of peptides, protein separated by at least one amino acid and other macromolecules such as polysaccharides or synthetic or natural polymers present in a preparation where said nanopore or nanotube is inserted into a lipid membrane which is subjected to a difference in potential greater than −160 mV, in a reaction medium comprising an alkali metal halide electrolyte solution with a concentration of less than 6M and at a temperature of less than 40° C., and where said use is intended to differentiate said peptides, proteins and other molecules according to their length and their mass.

According to one characteristic of the invention, the alkali metal halide is an alkali metal chloride represented by LiCl, KCl or NaCl.

According to another characteristic of the invention, the concentration of the electrolyte solution is of between 0.5 and 5M.

According to yet another characteristic of the invention, the concentration of the reaction medium in LiCl is equal to 1M or to 4M.

According to yet another characteristic of the invention, the difference in potential applied to the membrane is of between −80 and −10 mV, advantageously of −29 mV.

According to yet another characteristic of the invention, the temperature of the reaction medium is of between 3 and 33° C.

One particularly advantageous use of the invention lies in the characterization of the enzymatic degradation of a sample of peptides, proteins, polysaccharides of synthetic polymers by determination of the degradation products.

According to yet another characterization of the invention, the use is intended for the separation of the different sequences of peptides or proteins.

Another particularly advantageous use of the invention lies in the characterization of the natural or synthetic chemical modifications of native molecules such as a protein, a peptide, a metabolite, a medication.

Another particularly advantageous use of the invention lies in the characterization of the specific and molar enzymatic activity of an enzyme in a single prokaryote or eukaryote cell.

One particularly advantageous use of the invention lies in the characterization to identify and quantify so-called "metabolite" molecules from metabolic pathways or cell signalling.

The invention also relates to a peptide product obtained by the use of a nanopore constituted by a single peptide, such as peptide RR10.

A first advantage of the invention lies in the great sensitivity and high resolution of the technique which is able to differentiate between molecules that are very close to one another, different by one monomer.

Another advantage of the use according to the invention lies in the separation of the different peptide or protein sequences. Peptides, proteins, polysaccharides or synthetic polymers are present in a preparation presented as a pure biological or commercial complex mixture.

This, the invention enables a resolution to a level with an amino acid, a sugar or a monomer difference between two molecules.

Another advantage of the invention lies in the fact that this great sensitivity enables an analysis to be made from a very small sample.

Another advantage of the present invention lies in the numerous applications it offers such as the performance of peptide sequencing.

Another advantage of the invention lies in the possibility of being able to certificate as 100% pure a peptide or synthesized molecule.

Another advantage of the invention lies in the possibility of identifying and quantifying medications in all biological fluids, in a single cell.

Yet another advantage of the invention lies in its peptide identification capacity for biological medical diagnosis.

Yet another advantage of the invention lies in the possibility of preserving a peptide or a mixture of peptides, or a protein for an extended period by means of lyophilisation to obtain a powder.

This powder may then be inserted, protected by a film, to be used as a molecular code by way of a marker to identify it with total certainty to show its origin or its uniqueness, such as the production origin of a product, the certification of origin, etc. Lastly, inspection would be made by putting the powder into a buffer solution. A solution can be preserved at ambient temperature for several days to several months, for example at 4° C. the duration is of several months, at −20° C. the duration is of several years.

By peptide mixture is meant a well-defined mixture of, for example, 95% peptide at 10 AA and 5% at 8 AA. Each of the batches of these peptides may be chemically modified (phosphorylation, halogenation, ec.), this mixture being a preparation presented as a pure biological or commercial complex mixture.

It would be an invisible, and thus discrete, molecular code that may be read by re-suspending the peptide mixture and by decoding it using the technology described herein.

BRIEF DESCRIPTION OF THE DRAWINGS

Other characteristics, advantages and particulars of the invention will become more apparent from the additional description given herein in reference to the drawings, in which:

FIG. 9 shows a variant embodiment of that shown in FIG. 7.

DETAILED DESCRIPTION OF EMBODIMENTS

As follows from the above, it is now possible, in accordance with the use and the process according to the invention, to detect by means of an electrical measurement, individual peptides and to distinguish peptides of different sizes at single amino acid-level resolution. The same applies to the detection of a great number of molecules such as proteins, polysaccharides or synthetic or natural polymers present in a preparation.

In the remainder of the description given hereafter, by way of illustration the implementation will be described of a commercially-available product containing peptide RR10 given as pure so as to determine its exact composition.

Figure 1:
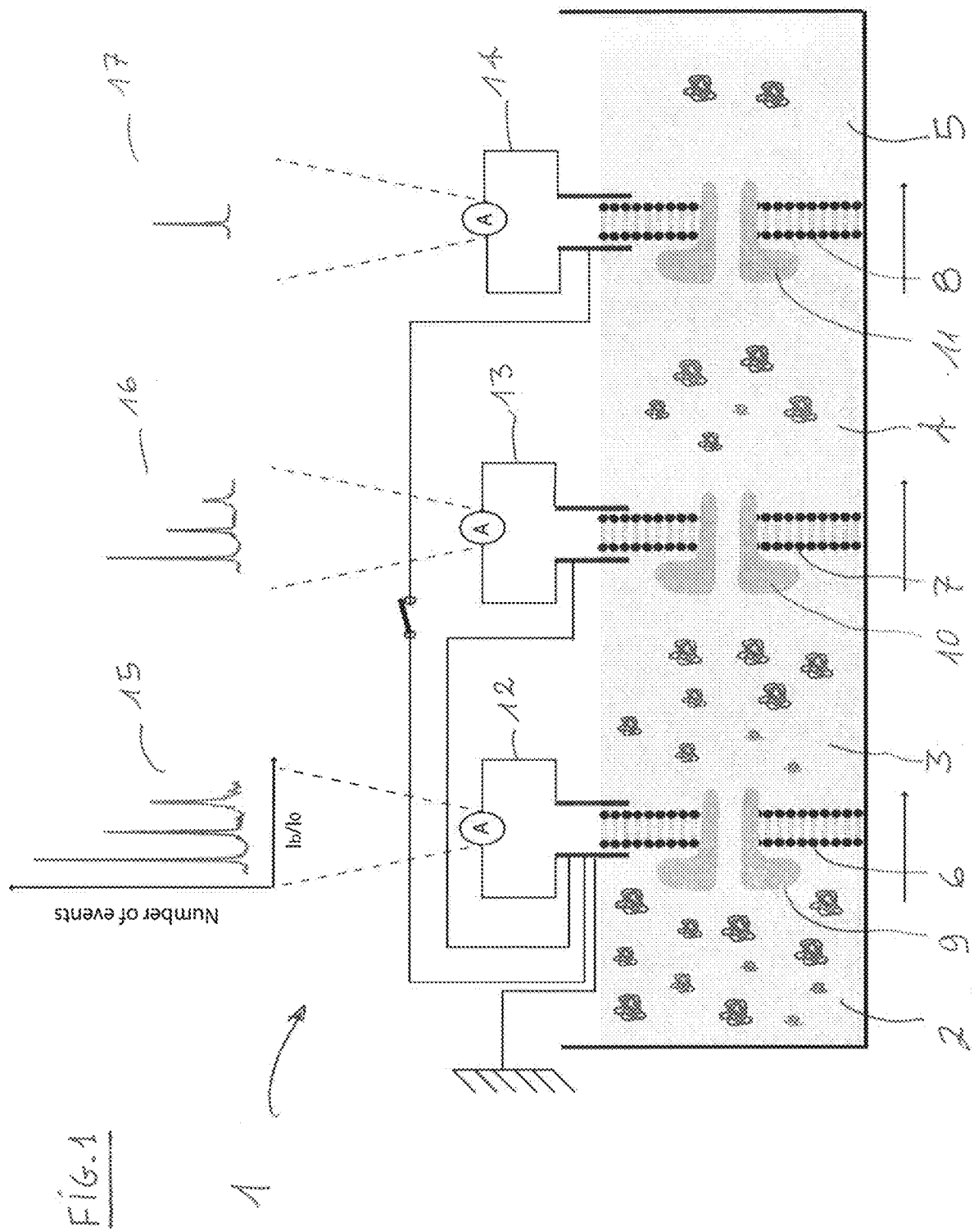
FIG. 1 shows one embodiment of a device to implement the invention.

FIG. 1 shows an example embodiment of a device 1 enabling a commercial or other product, of the type protein, polysaccharide or synthetic or natural polymers contained in a mixture, to be sequenced. It goes without saying that for each category of product the operating conditions are adapted according to the research criteria.

Device 1 comprises, for example, four compartments in series 2, 3, 4 and 5 separated from one another by three lipid membranes 6, 7 and 8 in which the aerolysin nanopores or nanotubes, respectively 9, 10 and 11 are inserted.

Membranes 6, 7 and 8 are subjected to an electrical current by means of circuits, respectively 12, 13 and 14. Thus, each membrane may be subjected to a current level according to operational conditions.

Device 1 according to the invention enables the translocation of molecules in the different compartments 2 to 5 to be monitored in real time.

Naturally, each electrical circuit 12, 13 or 14 is connected respectively to an electrical detector enabling the passage of each molecule containing the product to be analysed. In this example, it is a sample of peptides. As can be seen, the membrane 6 enables three pictograms to be drawn, respectively 15, 16 and 17. Pictogram 15 enables three peaks corresponding to three peptides to be identified, pictogram 16 shows two interesting peaks of two peptides and pictogram 17 a single peak or a single peptide.

Translocation to compartment 5 is stopped by the opening of the electrical circuit 14 to remove the pure peptide present in this compartment.

Pictograms 15, 16 and 17 shown in FIG. 1 correspond to the analysis of a peptide product whose specific experimental conditions are given hereafter. It goes without saying that device 1 is operational when analysis is made of a product constituted by proteins, polysaccharides or synthetic or natural polymers. It further goes without saying that the number of peaks depends on the nature of the original product.

A study will now be made of a commercial product given as pure to 96%, peptide RR10. The exact knowledge of its composition and the nature of its impurities is an important element in human medicine and one to which specialists are greatly attached.

By way of example, analysis has been made in the following manner of a commercially-available product, presented as constituted by peptide RR10 pure to 96%, so as to determine the exact chemical composition of its impurities.

The installation is analogous to that shown in FIG. 1, possibly reduced to two compartments. In that case, a lipid membrane, for example membrane 6 containing an aerolysin nanopore 9, is placed in a reaction medium having a lithium chloride concentration of 4M, a temperature of 5° C., and the membrane is subjected to a potential difference of −29 mV. Thanks to an extremely sensitive electrical detector, the electrical current travelling through the pores is measured.

The difference in potential causes the circulation of ions from the electrolyte between the two sides of the membrane, for example in compartments 2 and 3, thereby creating a measurable current. When the molecules pass through the nanotube, they interrupt the current. These interruptions are proportional to the size of the molecules and vary according to the concentration conditions, the pH and temperature of the reaction medium.

Figure 2:
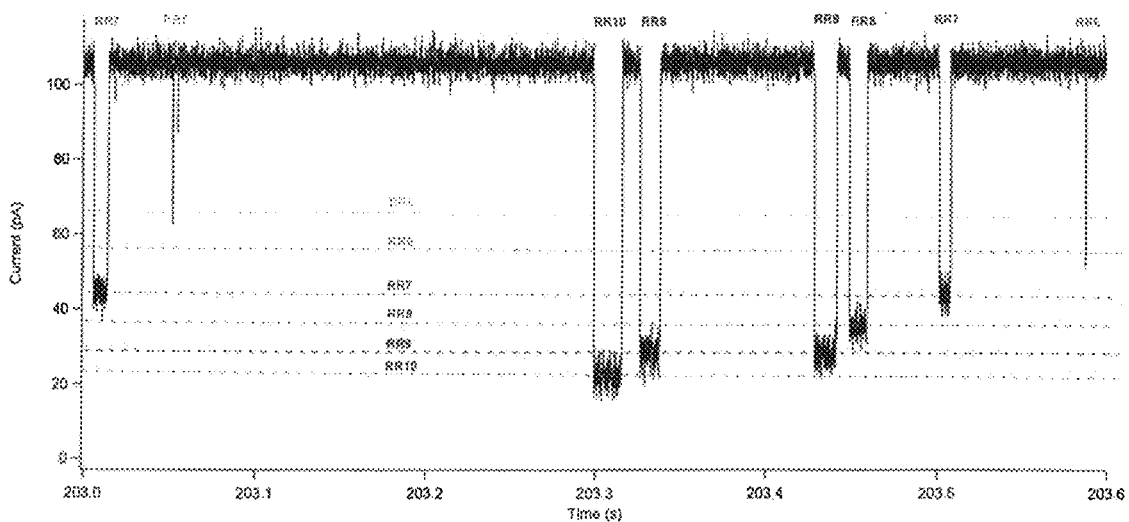
FIG. 2 shows the variation in the difference in potential according to the elution time corresponding to the detection of a peptide.

The current I is constantly monitored over time and FIG. 2 shows the starting current I0 when the ions circulate obstacle-free and current Ib when a blockade of the nanopore is occurring. The current loss corresponding to the different peptides composing the mixture presented as pure can clearly be seen. These impurities can be seen to be sub-products of the peptide RR10 synthesis process, incomplete peptides each having a specific moment of passage as well as a characteristic current loss staggered, as explained previously, from 30 to 68 pA.

FIG. 2 shows different signatures at different current levels. Thus, for an experiment time of 203.3 s at a voltage of 25 pA, a current loss is detected that corresponds to peptide RR10. As can be seen, the measurement performed reveals the presence of impurities constituted by peptides RR9, RR8, RR7, RR6 and RR5 at current values of between 30 pA and 68 pA.

Figure 3:
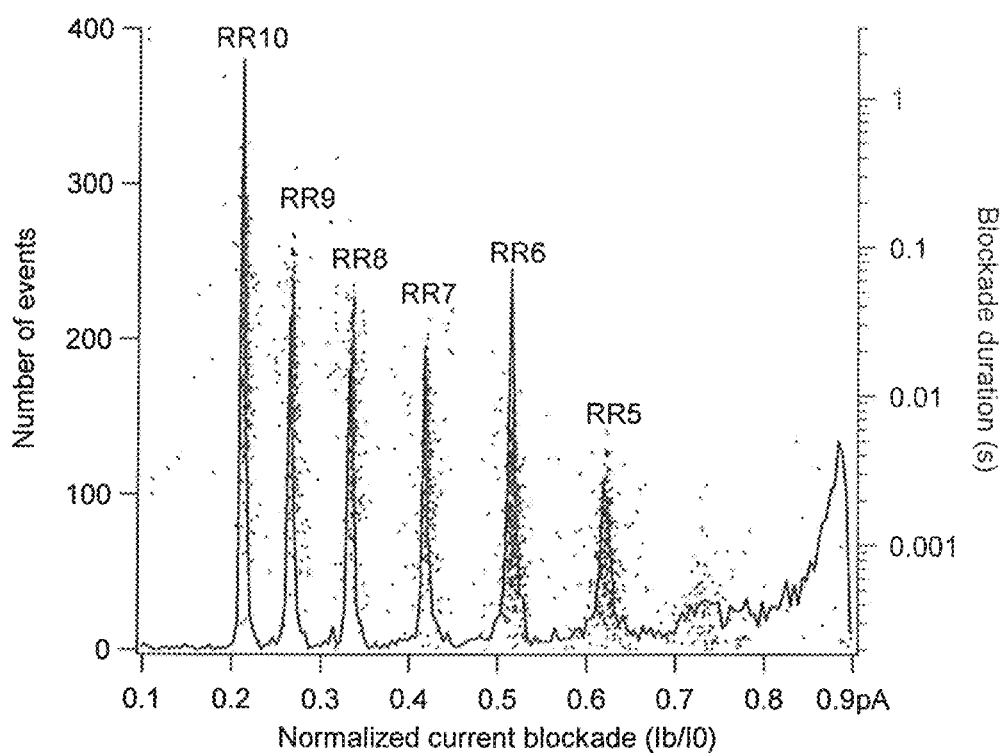
FIG. 3 shows the analysis of a mixture of six peptides.

From these measurements, the mass spectrogram shown in FIG. 3 has been constructed at the single-molecule scale. As can be seen, in the sample analysed, the peptide RR10 given as pure to 96% is however accompanied by several other peptides. These have been determined to be peptides RR9 and RR5.

The use of the nanopore according to the invention enables very high sensitivity to be achieved able to reveal the present of quantifiable peptide fragments (of the magnitude of 1% of the total number of molecules detected, in other words a few tens of molecules) in a sample sold as pure to 96%. To date, it is impossible to identify these fragments by classical mass spectrometry or by HPLC chromatographic analysis of the composition supplied by the vendor of this sample.

The advantage of the invention may be easily understood in that it enables a detection level of peptides, proteins, polysaccharides and synthetic polymers and other molecules to be reached that is impossible using classical analysis techniques.

So as to obtain satisfactory resolution and sensitivity, different factors must be taken into consideration.

Several trials have thus been made varying the physical-chemical conditions in the reaction medium: the electrolyte concentration, the nature of this electrolyte, the temperature of the medium and the potential difference applied to the membrane. It has thus been observed that an increase in the electrolyte concentration and a reduction in the temperature favour the detection of the shortest peptides and vice versa. The same goes for other molecules.

Indeed, as can be seen from the three graphs in FIGS. 4a-4c, reducing the temperature and increasing the electrolyte concentration of the reaction mixture leads to better resolution for small-sized peptides. In the graph of FIG. 4a, where the temperature is of 20° C. and the electrolyte concentration is of 2M, the resolution can be seen to be weaker for the smallest sizes: the peaks are not clear and there is a dense dispersion of events. In the graphs of FIGS. 4b and 4c, where the electrolyte concentration has been considerably increased (4M) and where the temperature has been reduced (5° C., graph of FIG. 4c), the definition for high values of Ib/I0, that is for the smallest peptides, is better. The events are clearly separated into two distinct peaks.

Thus, FIGS. 4a-4c show the results obtained by varying the temperature and the electrolyte concentration. The current blockade duration has been shown as a function of Ib which is the current intensity of the blockaded channel of the aerolysin nanopore and I0 the intensity of the current of the same empty channel of the nanopore.

With regard to FIG. 4a, the temperature is of around 20° C. and the electrolyte concentration of 2M. In FIG. 4b, the temperature is of around 20° C. and the electrolyte concentration of 4M. On the bottom curve of FIG. 4c, the temperature is of 5° C. and the electrolyte concentration of 4M.

It has been determined that the electrolyte concentration may be between 0.5 and 5M and that a concentration of 1M forms a good compromise, for example with electrolyte LiCl.

Different electrolytes have been used, such as, for example: LiCl, NaCl, KCl or KBr, RbCl, CsCl, KF, or ammonium chloride, tetramethylammonium chloride, etc. The results obtained are globally of the same magnitude whatever the electrolyte.

Thus, the electrolyte of a higher concentration enables molecules of lower molecular mass to be studied, of an order of magnitude of two amino acids, and surprisingly a single amino acid. In these conditions, the signal/noise ratio is better and the Ib/I0 values tend to the left of the spectrogram. Indeed, the closer the Ib/I0 ratio is to 0, the longer the molecule in question. This tendency leftwards induces a margin to the right of the spectrogram thereby favouring the detection of peptides whose length is less than three amino acids. Given the right margin of the spectrogram and the strong concentration of salt, the detection of a single amino acid is accessible.

With regard to the temperature, the study of the three diagrams of FIGS. 4a-4c show that the position of the peptides varies along the vertical axis and that it is more advantageous to have a temperature of 5° C. and a concentration of 4M. The resolution is thus improved. Generally, the temperature of the reaction medium may be between 3 and 33° C.

Figure 4:
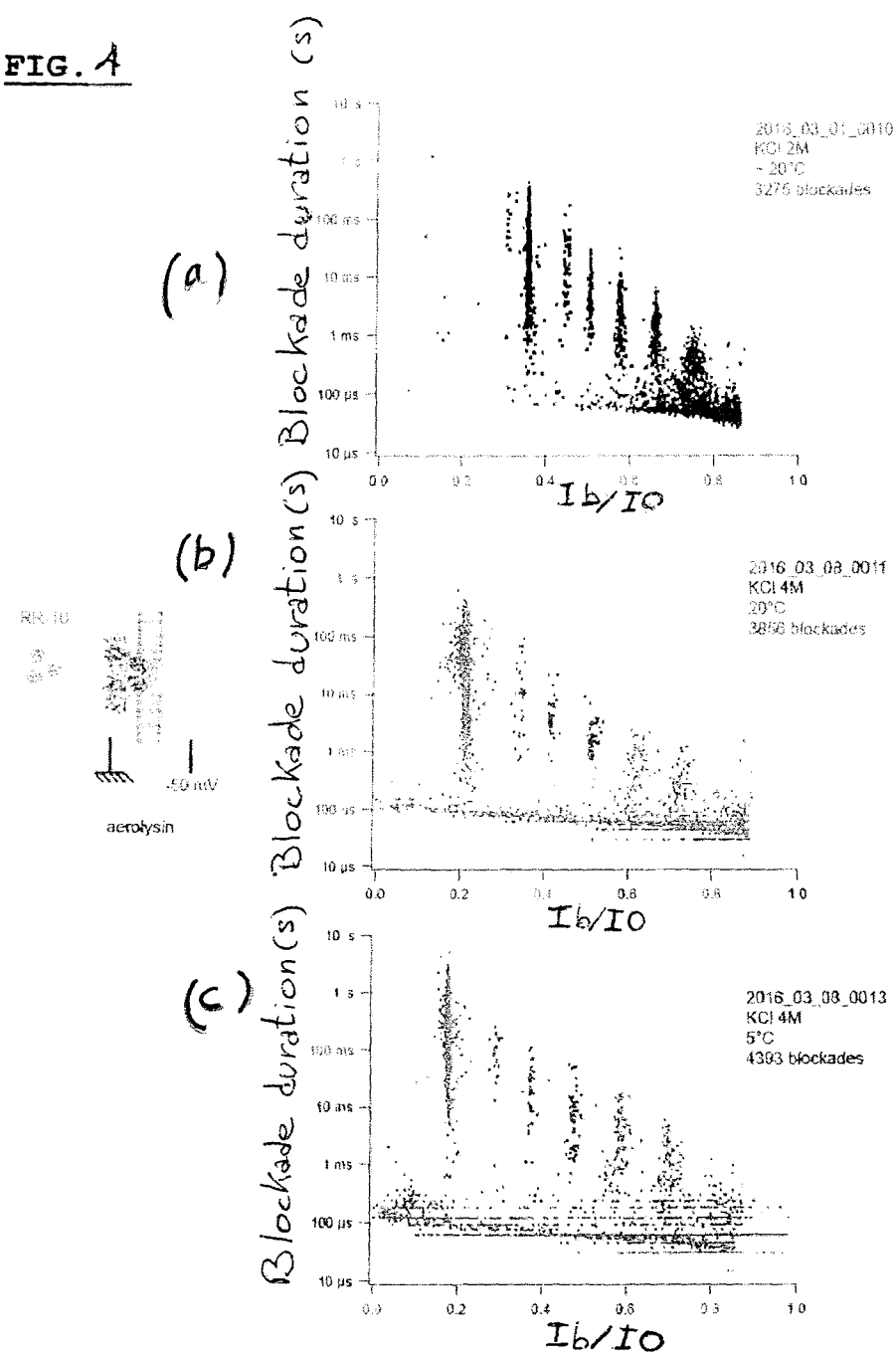
FIGS. 4a-4c show the analysis results for a commercially-procured sample of peptides.

The potential difference applied to the aerolysin nanopore membrane does not seem to have an effect on the position of the lines in the graphs in FIG. 4. However, going from −10 mV to −80 mV, it can be observed that the mean current blockade duration depends on the voltage for the peptide RR10 sample. The choice of current value thus depends on the resolution the user wishes to obtain. A potential difference of −29 mV applied to the membrane enables excellent resolution to be obtained.

In the above, an aerolysin nanopore has been implemented, but is goes without saying that other nanopores may be used. Thus, a nanopore or nanotube of the cyclodextrin type may be implemented in the process according to the invention by easily adapting the conditions of use, which is to say the temperature, the concentration in salt and the nature of the electrolyte.

The conditions of analysis of the peptide sample largely described above are applicable to other protein samples, regarding the nature of the electrolyte and its concentration, regarding the temperature of the reaction medium and the current level applied to the nanopore or nanotube. It goes without saying that these conditions are adapted according to the nature of these molecules and one skilled in the art has the necessary elements to define by means of simple trial those applicable to proteins, oligosaccharides or synthetic or natural polymers. By way of illustration, it has been determined that the longer the molecule in question, the more this length induces an Ib/I0 ratio that is close to 0.

Another advantage of the invention relates to enzyme reactions. It is known that numerous enzyme reactions are decisive in quantifying a product that is important for the diagnosis of an illness or for an industrial process. It is thus possible, in accordance with the invention, to monitor the enzyme degradation of a peptide, for example by trypsin, and the kinetic constants have been well determined. Naturally, one skilled in the art, may perform the degradation of a protein, a polysaccharide or synthetic or natural polymer by making certain adaptations and a few trials.

Figure 5:
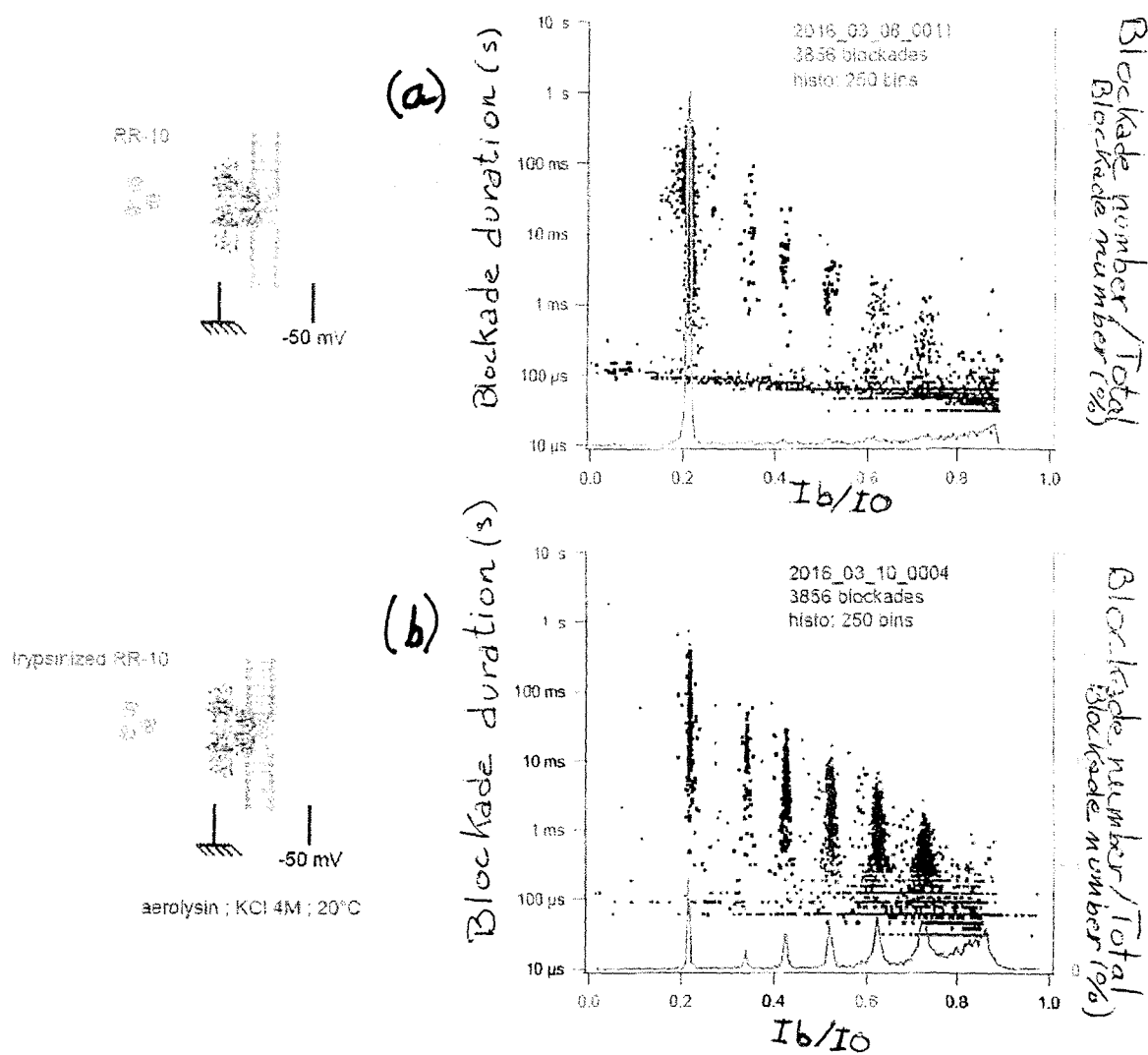
FIGS. 5a-5b show the enzymatic degradation of a peptide sample of 10 amino acids by trypsin.

FIGS. 5a-5b illustrate the results obtained by performing an analysis in accordance with the invention before (graph of FIG. 5a) and after (graph of FIG. 5b) enzyme degradation by measuring the current intensity Ib of the blockaded channel and the current intensity 10 of the same channel of the sample given as pure to 96%. In these diagrams, the line furthest to the left represents the peptide RR10, the other peptides being in trace form.

The first diagram shows that, before degradation, peptide RR10 is the principal constituent of the sample. After degradation by trypsin, the depletion in peptide RR10 occurs to the benefit of the other peptides RR9, RR8, RR7, RR6 and RR5.

The use of a nanopore or a nanotube in accordance with the invention thus enables the degradation by trypsin of peptide RR10 into shorter peptides RR9, RR8, RR7, RR6 and RR5 to be visualised. Consequently, the same process may be used to monitor other enzyme degradation processes for proteins, polysaccharides, synthetic or natural polymers or other macromolecules likely to interest a user (medication, industrial products or other).

Furthermore, peptide RR10, RR9, RR8, RR7, RR6 and RR5 are clearly distinguished. Peptides may thus be differentiated that differ by only one amino acid. This characterisation of the invention enables the extremely close and specific monitoring of chemical processes.

In the example, a peptide is referenced that is 10 amino acids in length, but it goes without saying that the invention may be used for longer peptides: 20, 50 or 100 amino acids, as well as for macromolecules of other types (proteins, polysaccharides, synthetic or natural polymers).

Figure 6:
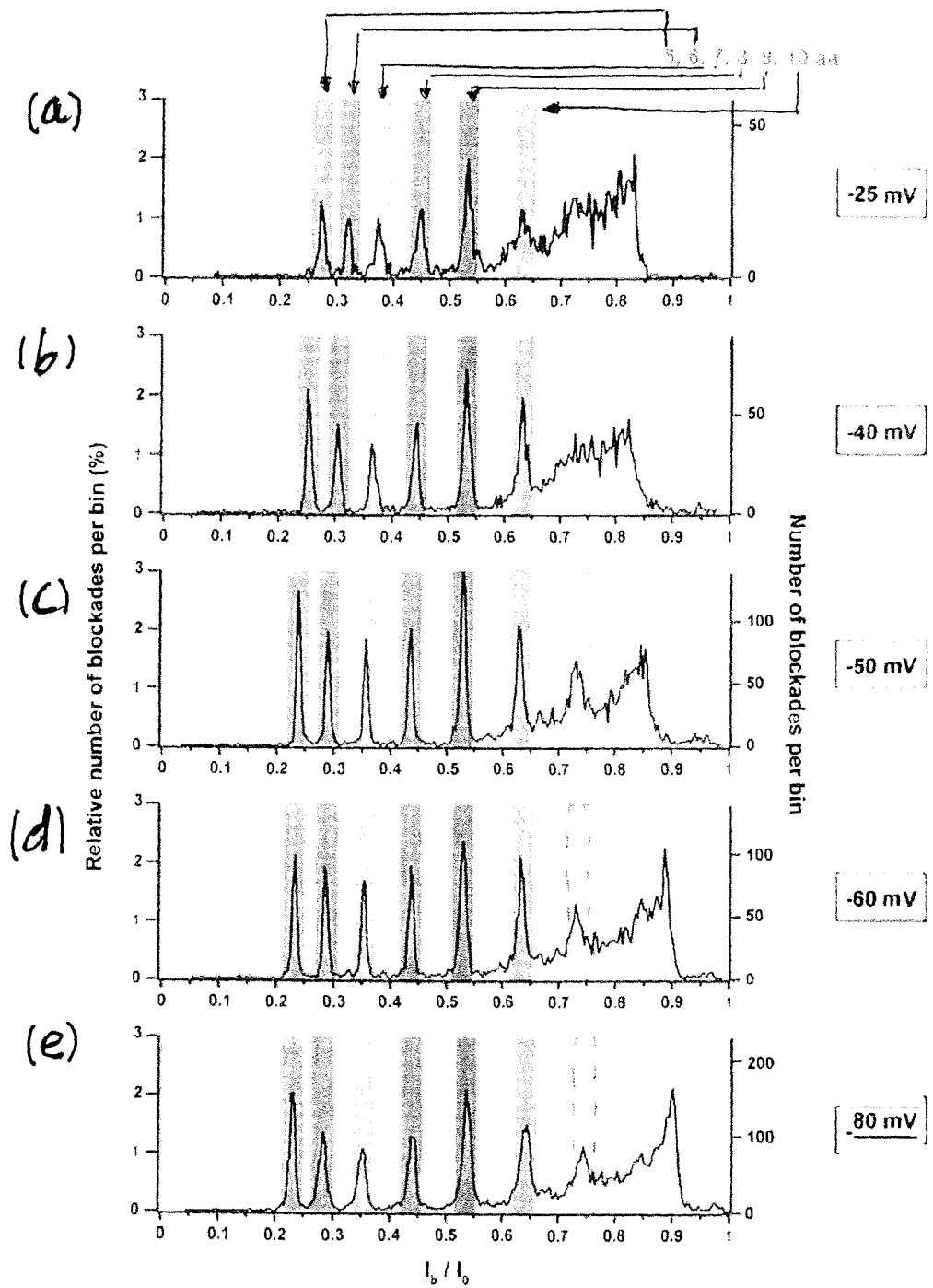
FIGS. 6a-6e show the detection of the peptides according to the variation in potential difference.

FIGS. 6a-6e show 5 histograms illustrating the effect of the voltage on the discrimination of arginine peptides of different lengths. These bar charts show the blockade current values Ib/I0 in the case of the interaction of the aerolysin nanopore with an equimolar mixture of arginine peptides of different lengths (5, 6, 7, 8, 9 and 10 amino acids) at −25 mV (FIG. 6a), at −40 mV (FIG. 6b), −50 mV (FIG. 6c), −60 mV (FIG. 6d) and −80 mV (FIG. 6e). The measurements are conducted in a medium of KCl 4M at pH 7.5 and at 20° C.

It is to be noted that 6 populations of peptides corresponding to 6 different peptide lengths of 5 to 10 amino acids are distinguished for a voltage of less than −50 mV (graphs of FIGS. 6a and 6b). However, for a voltage of greater than or equal to −50 mV, a $7^{th}$ population is identified which is shown in dotted lines (graphs of FIGS. 6c, 6d, and 6e).

Thus, the process according to the invention allows the fine analysis of molecule samples such as peptides by distinguishing one peptide from another by the presence of a single amino acid. Moreover, all the sequencing trials described above and validated were performed on very small quantities of peptides or proteins, which is from a few tens of molecules, for example, 2 to 15 tens of molecules.

The preceding work was performed with particular attention to samples given as pure to 96% so as to illustrate the invention. However, the separation of peptides of different lengths is obtained when the peptide sample is fully lodged in the nanopore and each monomer (amino acid) contributes to the current blockade. It can be understood that there is no limit to peptide sample analysis as long as the size of the nanopore receiving the peptides is adjusted.

The different fractions of peptides merely have to be collected following a process analogous to that implemented in chromatography so as to isolate a pure quantity of single peptide as explained with reference to FIG. 1.

The application has been amply illustrated by the study of a sample given as pure of peptide RR10. It goes without saying that the invention is implemented to characterise any peptide given as pure. Thus, peptides of a larger size such as peptides RR20, RR50 or R80 have been characterised. This thus presents a major advancement in the specific knowledge of samples used in medicine.

Furthermore, the invention may be applied to the study of samples comprising several peptides of the same length, but of different sequences, as shown in FIGS. 7a-7d.

Figure 7:
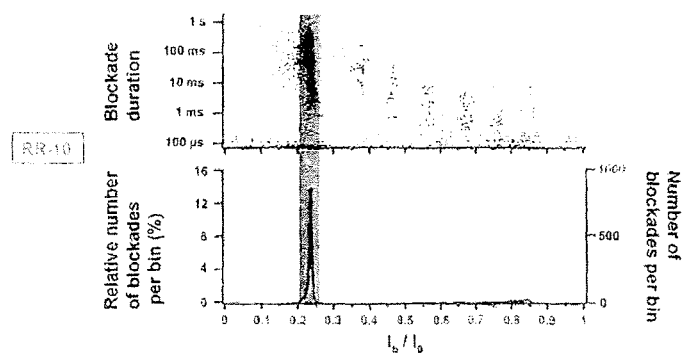
FIGS. 7a-7d show the discrimination of peptides 10 amino acids long, having different sequences.
Figure 7:
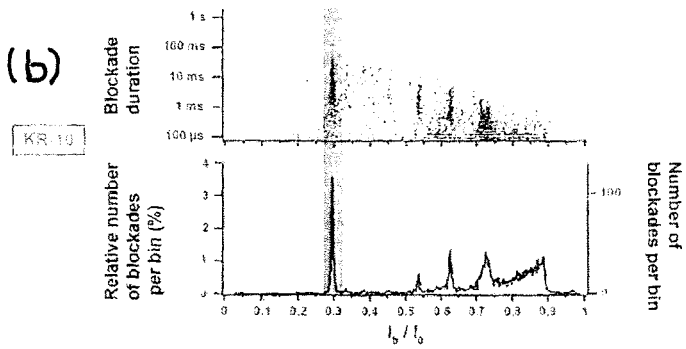
Figure 7:
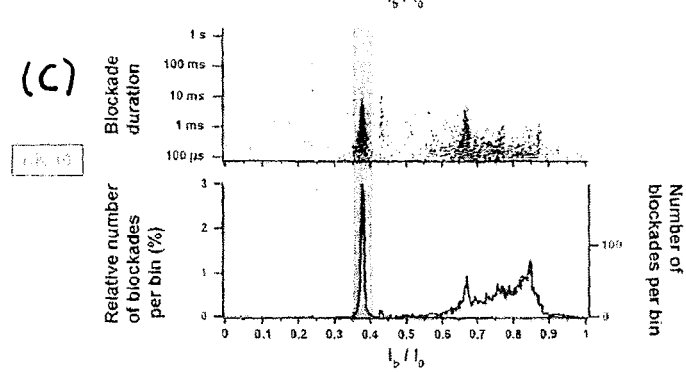
Figure 7:
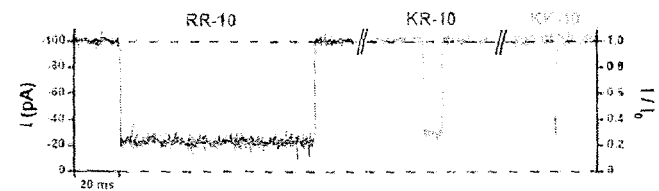

To do this, according to the same protocol as described previously, high purity (over 98%) samples were studied of 10 amino acids long (RR10) arginine peptide, shown on the graphof FIG. 7a, and 10 amino acids long (KK10) lysine peptide, shown on the graph of FIG. 7b. It can be seen that the majority populations identified differ both in terms of Ib/I0 ratio value and mean blockade duration. This reveals that the invention enables homopeptides of the same length but different sequences to be differentiated.

Moreover, a high purity sample (over 98%) was tested of a heteropeptide composed of 5 lysine amino acids and 5 arginine amino acids (KR10), shown on the graph of FIG. 7c. The graph of FIG. 7c clearly shows that this sequence corresponds to a nanopore blockade profile, in terms of duration and intensity, different from the other peptides.

The graph of FIG. 7d shows the typical blockade created by three peptides over time.

The invention is thus also able to discriminate between peptides of the same length, and peptides of different sequences, thereby opening new perspectives for biological and medical analysis.

The invention has a particularly important application in metabolomics and enzymology.

Biological medical diagnosis is obliged to evolve today so as to be able to work with precious and rare samples containing only a few cells or microvesicles of interest, or else small sample amounts such as those from a mouse.

Classical determination methods that use luminescent spectrometry, absorption or fluorescence, require large sample amounts to obtain a significant signal, detached from the background noise. For example, a minimum of 500,000 white blood cells is needed for the determination of the activity of the enzyme complexes of the respiratory chain. These classical methods, for example, make it impossible to perform an enzyme profile on an isolated circulating tumour cell in the blood.

A nanopore in accordance with the invention may also be used to separate the different sequences of peptides or proteins. The sequence of a peptide conditions its physical-chemical properties, which in turn conditions its passage through a nanopore. Indeed, the nature of amino acids conditions peptide conformation. Different forms of protein pass through the nanopores at different speeds. Similarly, the other properties of proteins (charge, hydrophobia, etc) influence the speed and frequency of their passage through a nanopore, and thus the current blockade characteristics they induce. Consequently, it is possible, thanks to the use of a nanopore according to the invention, to identify different proteins present in a mixture, differing by their size but also by their sequences.

To do this, a mixture of proteins to be separated and identified is placed in appropriate conditions and passed through the nanopore. Each protein creates a specific signature in terms of specific current blockade duration and current blockade amplitude, since it has particular properties of duration, intensity and moment.

It is also possible for a nanopore according to the invention to be used to characterise the natural or synthetic chemical modifications of native molecules such as a protein, peptide, metabolite or medication.

The chemical modifications to which a molecule is subjected change is characteristics: size, conformation, charge, hydrophobia, etc. As already explained above, these are characteristics that influence the passage through the nanopore and consequently the current blockades caused by this passage.

The aerolysin nanopore technology perfected in the invention enables the activity of a small number of enzyme copies in a single cell to be quantified according to an industrial process, enabling the enzyme activity of a small number of enzyme molecules to be quantified after lysis of the original cell.

Even the most sophisticated methods such as tandem mass spectrometry require a minimum of 50,000 cells. This is why the inventers turned towards the development of a "nanopore" technology enabling the activity of a small number of enzyme copies in a single cell to be quantified.

Figure 8:
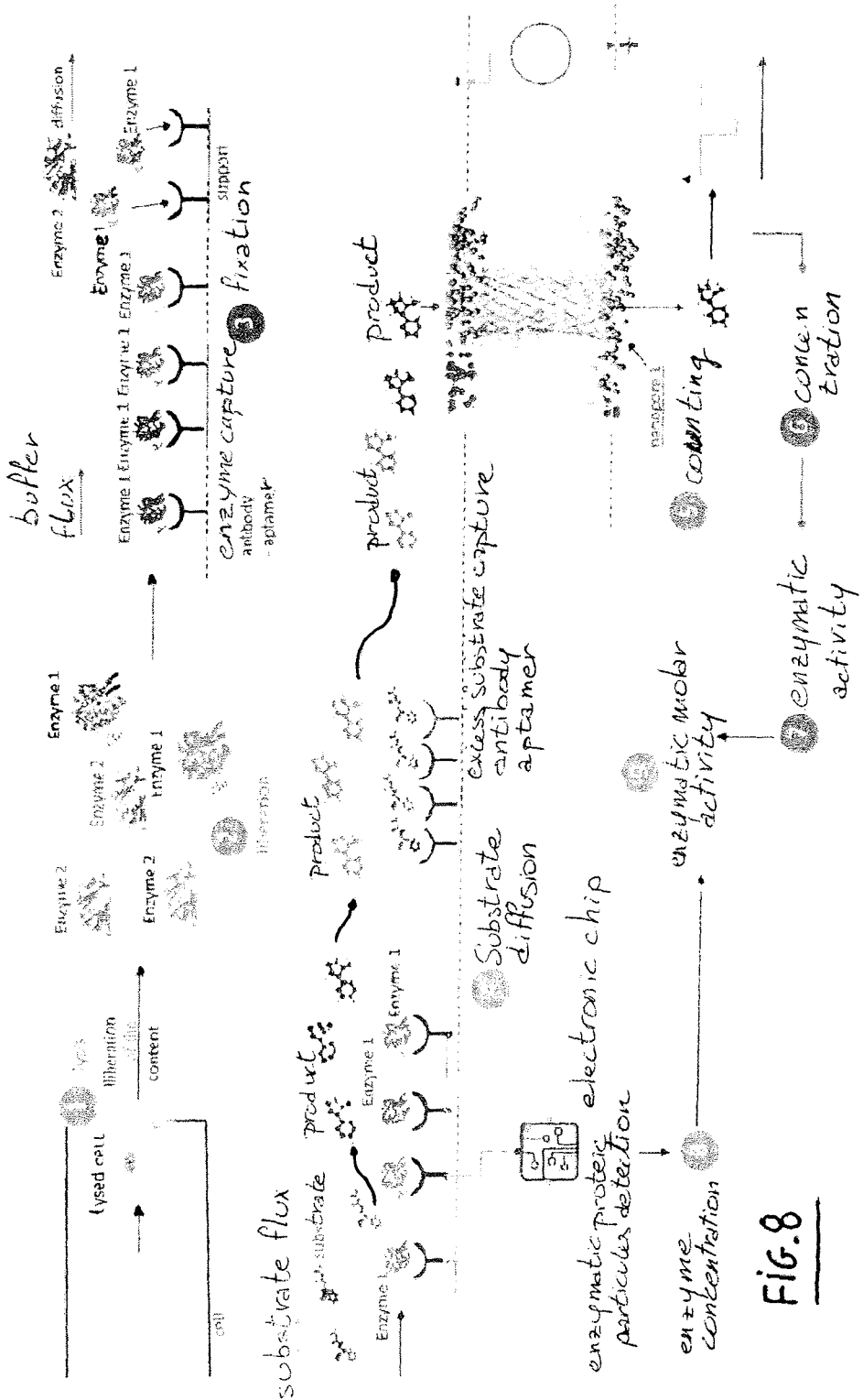
FIG. 8 shows the detection of an enzymatic activity from a single cell or vesicle.

FIG. 8 shows an example of a possible industrial process enabling the enzyme activity of a small number of enzyme molecules released after lysis of the original cell to be quantified. This specific detection and quantification system thus enables quantifications to be made on single cells which up to now have been impossible to perform. Its use in the medical domain opens up a wide field of application, namely that of personalised medicine.

This process is, for example, the following one illustrated in FIG. 8, which represents a block diagram of the microfluidic system enabling the quantification of a specific enzyme activity wherein the enzyme is brought to the pore inlet by microfluidic guidance.

In 1 of FIG. 8, the cell is lysed in a classical manner to release its enzyme content. The single cell may be of the prokaryote or eukaryote type.

In 2 of FIG. 8, the molecules of the enzyme of interest and other molecules released from the lysed cell are driven by the flow of a buffer solution in the tubes of the microfluidic system (system to handle fluids whose volume is of $10^{-9}$ to $10^{-18}$ litres) up to a reaction chamber.

In 3 of FIG. 8, in the reaction chamber the molecules of the enzyme of interest are captured and fixed to a support by specific probes that may be anti-bodies, aptamer probes, specific peptides, etc. The continuous buffer flow solves the problem of diffusion. The other molecules are eliminated by diffusion.

In 4 of FIG. 8, the specific substrate of the enzyme of interest is then injected and captured by the enzymes of enzymes of interest fixed on the support. These enzymes transforms the substrate into a product which is in turn diffused in the buffer. Any substrate excess is captured by the specific downstream probes.

In 5 of FIG. 8, finally, the product molecules pass through a series of aerolysin nanopores.

In 7 of FIG. 8 and 8 of FIG. 8, each passage is detected and enables each molecule to be counted and its enzyme concentration and activity to be deduced. The enzyme concentration is determined by an electronic system.

This quantification of the number of enzyme molecules combined with that of the product enables, in 9 of FIG. 8, a highly-precise molar enzyme activity to be obtained.

Using the same process, it is possible to identify and quantify the so-called "metabolite" molecules belonging to metabolic pathways and playing a part in cellular signalling.

Similarly, a cell lysate is treated to obtain is composition. Enzyme substrates or ligands peculiar to the biological process being studied enable only those molecules involved in the processes in question to be detected.

These molecules, called metabolites, are generally produced by enzymes belonging to cellular biochemical pathways such as the KREBS cycle, the pentose phosphate pathway, etc. These metabolites are very often in turn substrates and products of enzyme reactions that are bound in a chain to one another in cellular metabolic pathways. For pentose phosphate pathways, these metabolites are, for example, glucose-6 phosphate, 6-phosphogluconate or glyceraldehyde-3-phosphate. In the KREBS cycle, the metabolites are, by way of example, citrate, succinate or alpha-ketoglutarate. The concentration of these metabolites varies according to the cellular homeostasis and more particularly in the case of a pathology. In a single cell, these metabolites are in quantities that cannot be detected by existing quantification techniques. In addition to the metabolites described above, our invention also enables the quantification of hormones, neuromediators, neurotransmitters, or of molecules present in cell signalling pathways or messaging pathways such as ATP, ADP, AMPc, IP3, or arachidonic acid.

FIG. 9 shows a variant embodiment of the system shown in FIG. 8. The detection and electronic quantification of the enzyme molecules in 8 of FIG. 8 may be replaced by the nanopores in 5 of FIG. 8 after all the extraneous substrate molecules have been eluted and the product molecules counted. Several flushing/rinsing cycles are performed gently so as not to elute the enzyme molecules caught on their specific probes in 4 of FIG. 8 with the substrate and product molecules. When the micro-capillary has been rinsed, the elution of the fixed enzyme molecules, in 4 of FIG. 8, is performed. These enzyme molecules are then counted in 5 of FIG. 8 by the nanopores that were used previously to count the product molecules.

In 5a of FIG. 9, the excess substrate is rinsed in a buffer flow. The nanopore transfer current is cut off. The elution and rinsing conditions are such that they enable the enzyme molecules to remain fixed to their specific probes. In 6a of FIG. 9, the elution conditions are more drastic and enable the enzyme molecules to leave their specific probes and diffuse through the nanopores after the passage current has been switched back on.

The Figures above 8 and 9 also illustrate the principle of the invention in the qualitative quantification of metabolites and the determination of the molar enzyme activity for any enzyme.

In the process in FIGS. 8 and 9, the enzyme protein molecules may merely be replaced by metabolites and the processes simplified to eliminate the enzyme capture step.

The invention claimed is:

1. A process for electrical detection of one or more peptides or proteins present in a preparation, the process comprising:
    providing the preparation to a reaction medium in contact with an aerolysin nanopore or nanotube inserted into a lipid membrane; and
    applying a difference in potential that is greater than −160 mV to the lipid membrane to differentiate the peptides or proteins by length and/or mass for purposes of electrically detecting the peptides or proteins,
wherein:
    the peptides or proteins each consist of an amino acid sequence having from 5 to no more than 100 amino acid residues;
    the reaction medium comprises an electrolyte solution of an alkali metal halide with a concentration of at least 2M and less than 6M; and
    the reaction medium is at a temperature of less than 40° C.

2. The process according to claim 1, wherein the alkali metal halide is an alkali metal chloride.

3. The process according to claim 1, wherein the alkali metal halide is KCl or NaCl.

4. The process according to claim 1, wherein the concentration of the alkali metal halide is between 2M and 5M.

5. The process according to claim 1, wherein the alkali metal halide is LiCl.

6. The process according to claim 1, wherein the difference in potential applied to the lipid membrane is between −80 and −10 mV.

7. The process according to claim 6, wherein the difference in potential applied to the lipid membrane is −29 mV.

8. The process according to claim 1, wherein the temperature of the reaction medium is between 3 and 33° C.

9. The process according to claim 1, wherein the process is performed to determine degradation products of an enzymatic degradation of a sample of the peptides or proteins.

10. The process according to claim 1, wherein the process is performed to separate different sequences of the peptides or proteins.

11. The process according to claim 1, wherein the process is performed to identify a natural or synthetic chemical modification to the peptides or proteins.

12. The process according to claim 1, wherein the process is performed to quantify an enzymatic activity of an enzyme in a single prokaryote or eukaryote cell.

13. The process according to claim 1, wherein the process is performed to identify and quantify the molecules of a metabolite from a metabolic pathway or cell signalling.

14. The process according to claim 1, wherein a single peptide is detected and differentiated by length and/or mass.

15. The process according to claim 1, wherein RR10 is detected and differentiated by length and/or mass.

16. The process according to claim 1, wherein the one or more peptides are detected and differentiated by length and/or mass.

17. The process according to claim 1, wherein the one or more proteins are detected and differentiated by length and/or mass.

18. The process according to claim 1, wherein the process has a resolution of one monomer in differentiating the peptides or proteins.

19. The process according to claim 1, wherein the alkali metal halide is KCl with a concentration of 4M in the reaction medium.

20. The process according to claim 1, wherein the temperature of the reaction medium is between 3 and 20° C.

* * * * *